United States Patent [19]
Desai et al.

[11] Patent Number: 5,952,291
[45] Date of Patent: Sep. 14, 1999

[54] PROCESS FOR THE PREPARATION OF HIGH PURITY IMIDAZOLINE BASED AMPHOACETATE SURFACTANTS

[75] Inventors: Bharat Desai, Belle Mead, N.J.; Peter Lees, Birkenshaw, United Kingdom; Jean-Marc Ricca, Lyon, France; David J. Tracy, Plainsboro, N.J.

[73] Assignee: Rhodia Inc., Cranbury, N.J.

[21] Appl. No.: 09/055,368

[22] Filed: Apr. 6, 1998

Related U.S. Application Data

[62] Division of application No. 08/801,313, Feb. 18, 1997, Pat. No. 5,744,063, which is a continuation of application No. 08/135,094, Oct. 12, 1993, abandoned.

[51] Int. Cl.$^6$ ............................ B01F 17/00; B01F 17/22; B01F 17/32; C07D 233/04; C07D 233/14; C11D 1/88
[52] U.S. Cl. ........................... 510/500; 252/356; 252/357; 548/352.1; 562/564
[58] Field of Search ......................... 562/564; 548/352.1; 252/356, 357; 510/500

[56] References Cited

U.S. PATENT DOCUMENTS

| | | | |
|---|---|---|---|
| 4,044,034 | 8/1977 | Christiansen | 260/404.5 |
| 4,269,730 | 5/1981 | Wechsler et al. | 252/356 |
| 4,705,893 | 11/1987 | Sotoya et al. | 562/564 |
| 4,833,253 | 5/1989 | Ploog et al. | 548/352.1 |
| 5,491,245 | 2/1996 | Grüning et al. | 554/68 |
| 5,569,767 | 10/1996 | Uphues et al. | 548/352.1 |
| 5,744,063 | 4/1998 | Desai et al. | 252/356 |

FOREIGN PATENT DOCUMENTS

| | | |
|---|---|---|
| 0 040 346A1 | 2/1981 | European Pat. Off. . |
| 0269939B1 | 6/1988 | European Pat. Off. . |
| 0269940B1 | 8/1988 | European Pat. Off. . |
| 0373491 | 6/1990 | European Pat. Off. . |
| 2725780 | 6/1977 | Germany . |
| 3639752 | 5/1987 | Germany . |
| 3641871 | 6/1988 | Germany . |
| 4240154 | 1/1994 | Germany . |
| 4240154 | 6/1994 | Germany ............................... 552/564 |
| 4307 709 A1 | 9/1994 | Germany . |
| 61-143347 | 7/1986 | Japan ..................................... 552/564 |
| 930296 | 3/1963 | United Kingdom . |
| 2278 848 | 12/1994 | United Kingdom . |
| WO9210481 | 6/1992 | WIPO . |
| WO94/13621 | 6/1994 | WIPO . |

OTHER PUBLICATIONS

EPO Search Report for EP Counterpart of USSN 08/135,094.

*Primary Examiner*—Floyd D. Higel
*Attorney, Agent, or Firm*—Craig M. Bell

[57] ABSTRACT

Imadazoline-based amphoacetates of higher purity, containing essentially negligible amounts of unalkylated amido amines, lower amounts of glycolic acid salts and monochloroacetate salts, superior to currently available conventional amphoacetates, are provided. This is demonstrated by their improved surface-active properties. Lower inherent irritation properties may be expected due to improved purity.

The higher purity amphoacetates can be obtained via processes utilizing precise pH control during the reaction of imidazoline, or its open-chain derivatives, with alkylating agents, e.g. sodium monochloroacetate. The pH can be controlled by adding the base slowly or automatically in response to a pH metering device to maintain a constant pH, or by a series of staged additions which are calculated to maintain pH within a stated range. The reaction may also be carried out by conducting the initial hydrolysis of the imidazoline ring structure, followed by alkylation. These higher-purity amphoacetates contain essentially fully alkylated products and lower amounts of glycolic acid derivatives, even though a ratio of SMCA to substituted imidazoline, or its open-ring derivative, of less than 1.5:1.0 and close to 1.0:1.0 is used.

21 Claims, No Drawings

PROCESS FOR THE PREPARATION OF HIGH PURITY IMIDAZOLINE BASED AMPHOACETATE SURFACTANTS

RELATED APPLICATIONS

This application is a divisional application of U.S. application Ser. No. 08/801,313, filed on Feb. 18, 1997, now U.S. Pat. No. 5,744,063 which is a continuation of U.S. application Ser. No. 08/135,094, filed on Oct. 12, 1993, now abandoned.

The present invention relates to higher purity imidazoline based amphoacetate surfactants characterized by improved compositional consistency, mildness and surface activity and improved processes for the preparation thereof.

STATEMENT RELATING TO THE PRIOR ART

Imidazoline-based amphoacetate surfactants are widely used as the surface active base for cosmetic formulations such as shampoos, cleansing detergents and the like as these products are known for their mildness, safety and lack of irritating effects to skin and eyes.

Amphoacetate surfactants derived from imidazolines are a class of surfactants characterized by the presence of incipient positive and negatively charged sites. Thus, depending on the pH of the medium, they may function as anionic, cationic or nonionic surfactants.

The amphoacetate surfactants exhibit excellent surface active properties such as surface tension reduction, lower pC-20 values (surface activity efficiency—amount of surfactant needed to lower the surface activity by 20 units), excellent foaming, wetting and the like. They are compatible with both cationic and anionic surfactants. Due to their biodegradability, lack of skin irritation and unique ability to reduce the irritancy of more aggressive surfactants, such as ether sulfates, the amphoacetate surfactants have gained wide use as secondary surfactants in the personal care industry. Furthermore, because of their hydrolytic stability, compatibility with electrolytes and excellent hydrotroping power, they are also used in household and industrial cleaner formulations.

There are several different types of imidazoline based amphoteric surfactants e.g. propionates, sulfonate and acetates. They are prepared by reacting an appropriate imidazoline derivative with a suitable agent containing the desired functional group. For example, amphoacetates can be prepared by:

1) forming a substituted imidazoline by reacting an aminoethyl alkanol amine or an ethylene alkylene triamine with a fatty acid:

FORMULA I $$RCO_2H + NH_2CH_2CH_2NH[(CH_2)_NX] \longrightarrow R-C\begin{array}{c}N-CH_2\\ \diagdown \ \ \ \ \ \ |\\ N-CH_2\\ |\\ (CH_2)_N-X\end{array}$$

2) hydrolyzing the imidazoline to an amido amine followed by (or simultaneously with) reacting those compounds with an alkylating agent such as monohaloacetic acid or its sodium salt in the presence of sodium hydroxide.

The reaction product contains no imidazoline structures though this specification will continue to use the art accepted terminology of imidazoline-based amphotoric surfactant.

It has been thought that imidazoline-based amphoteric surfactants may contain a mixture of different surface-active species. The following structures have been cited in literature:

AMPHOMONOACETATE

Formula II $$RC(O)-NH-CH_2CH_2-N-CH_2CH_2OH$$
$$|$$
$$CH_2C(O)ONa$$

(New Proposed Structure)

Formula III $$\begin{array}{c}CH_2C(O)O-\\|\\R-C-N+-CH_2CH_2OH\\|\ \ \ \ \ \ |\\N\ \ \ \ CH_2\\ \diagdown\diagup\\CH_2\end{array}$$

(Old Proposed Structure)

AMPHODIACETATE

Formula IV $$RC(O)-NH-CH_2CH_2-N-CH_2CH_2OCH_2C(O)ONa$$
$$|$$
$$CH_2C(O)ONa$$

Formula V $$RC(O)N-CH_2CH_2-N-CH_2CH_2OH$$
$$|\ \ \ \ \ \ \ \ \ \ \ \ \ \ \ \ \ \ \ \ \ \ \ |$$
$$CH_2C(O)ONa\ \ \ \ CH_2C(O)ONa$$

Formula VI $$\begin{array}{c}CH_2CH_2OH\\|\\RC(O)-NH-CH_2CH_2-N+-CH_2C(O)O-\\|\\CH_2C(O)ONa\end{array}$$

Formula VII $$\begin{array}{c}CH_2C(O)ONa\\|\\R-C-N+-CH_2CH_2OCH_2C(O)O-\\|\ \ \ \ \ \ |\\N\ \ \ \ CH_2\\ \diagdown\diagup\\CH_2\end{array}$$

(Old Proposed Structure)

The R group in these formulas represents coco or other suitable alkyl moieties.

Cosmetic Toiletry and Fragrance Association International Cosmetic Ingredients Dictionary describes amphoacetates and amphodiacetates as two distinct classes of imidazoline-based amphoteric surfactants. These are prepared by reacting an imidazoline under alkylating (carboxylating) conditions with either one equivalent (or slight excess) or two equivalents (or an excess) of an appropriate alkylating agent, e.g. sodium monochloroacetate. The corresponding alkyl chains can be coco, lauryl (coco or lauryl amphoacetates or diacetates) or selected from other fatty acids, as required by the specific application. Furthermore, since the starting imidazoline is unsymmetrical in nature, both types of derivatives may be produced from either of the possible amines resulting from the imidazolines. Thus, both structural types "primary amine/tertiary amide" and "secondary amine/primary amide" have been mentioned in the literature.

The alkylating agent, sodium monochloroacetate, commonly used for manufacture of both amphoacetates and diacetates, is a reactive chemical which, under reaction conditions may undergo a number of different types of reactions:

1. Reaction with amino functions of the imidazoline or hydrolyzed imidazolines to produce mono or polycarboxylated species.
2. Reaction with water to produce the corresponding glycolic acid derivatives or reaction with glycolic acid derivatives to produce diglycolates.

3. Reaction with hydroxyethyl groups of imidazoline derivative to produce the corresponding carboxymethyl ethers.

Of the above possible reactions, only "1" and "3" are expected to lead to the formation of the desired amphoteric species where reactions of type 2 form undesirable by-products (glycolates/diglycolates), thus reducing the amount of the alkylating agent available for the reaction.

Recently, based on the newly developed analytical methodology, it has been established that commercially available coco/lauro amphoacetates contain (in addition to sodium chloride) the following major organic components:
Amphoacetate (derived from secondary amine/primary amide, Formula II)
Corresponding unalkylated amido amine
Glycolate/diglycolate
Residual Sodium Monochloroacetate The above results are based on utilization of nuclear magnetic resonance spectroscopy ($^1$H, $^{13}$C), liquid and gas chromatography, ion-chromatography and capillary electrophoresis.

The following table shows the results obtained from analyzing three commercial amphoacetates:

|  | AMPHO-ACETATE | UNALKYLATED AMIDO AMINE RATIO | GLYCOLIC ACID (%) |
| --- | --- | --- | --- |
| COMMERCIAL PROD. I | 75 | 25 | 2.6 |
| COMMERCIAL PROD. II | 63 | 37 | 2.4 |
| COMMERCIAL PROD. III | 83 | 17 | 2.0 |

From the above results it can be seen that the commercial products all contain a significant amount of unalkylated material. The presence of unalkylated material has a negative effect on surface activity.

Excess sodium monochloroacetate also leads to the formation of by-product glycolic acid as sodium glycolate. This by-product is unacceptable because the glycolic acid does not contribute to the surface active properties of the desired compound.

U.S. Pat. No. 4,269,730 teaches a method for preparing amphoteric surfactants of increased purity by heating to a temperature of 70°–80° C., a mixture of substantially pure substituted imidazoline with 1.0–2.5 molar equivalents chloroacetate salt per imidazoline and water to a solids content of 20%–50% until the chloroacetate is substantially consumed; then adding 1.0–2.5 molar equivalents NaOH based on the chloroacetate salt and heating at from 70°–80° C. at least until substantially all the imidazoline rings are opened to form a clear aqueous solution of 15%–35% solids. Contrary to the teachings of this reference, it has been found that the product of this patent still contains amounts of by-products that affect the surface activity of the final product.

By careful control of reaction conditions, substantially fully alkylated imidazoline derived amphoacetate surfactants can be produced even when relatively low excess of sodium monochloroacetate over the imidazoline (1.0–1.5:1) is used. The products exhibit surface activity properties comparable to those presently provided by commercially available amphodiacetates but which contain much lower levels of sodium glycolate and sodium chloride. The products of the invention are, furthermore, substantially free of amido amines, as compared to conventional amphoacetates while containing comparable amounts of sodium chloride and lower amounts of glycolic acid derivatives. These higher purity amphoacetates exhibit superior surface active properties, compared to conventional materials.

SUMMARY OF THE INVENTION

In accordance with the invention, improved imidazoline based amphoacetate surfactants are provided which are characterized by higher purity, exhibiting improved surface activity as evidenced by improved foaming, wetting, detergency and higher surface tension reduction. These improved amphoacetate surfactants can be prepared by new processes which involve the use of controlled pHs during the entire reaction and particularly during the alkylation portion of the process. The pH can be controlled by adding an appropriate base such as sodium hydroxide slowly or automatically in response to a pH metering device to maintain a constant pH. This can also be accomplished by a series of staged additions of base, e.g., sodium hydroxide which are calculated to maintain the pH within the desired range. It has also been found that products of higher purity may be obtained by exposing the imidazoline to conditions which favor ring opening prior to alkylation followed by reaction with the alkylating agent, e.g., sodium monochloroacetate, under carefully controlled conditions. By conducting the reaction of imidazoline or its ring opened derivative with the haloacetic acid salt under controlled pH conditions, the yield of the alkylation reaction is substantially increased resulting in the formation of lower amounts of glycolic acid. Glycolic acid is formed from the haloacetate salt and is usually compensated for by excess acetate. The process of the invention allows for the use of lower molar ratios of substituted imidazoline, or its derivative to haloacetate salts, less than 1:1.5 and approaching 1:1. while still providing substantially fully alkylated product.

Careful pH and temperature control during the reaction allows the reaction to proceed with less sodium monohaloacetate salt resulting in a higher purity product (less by-product unalkylated amide, glycolic acid, NaCl and residue haloacetate salt). The products of the invention exhibit superior surfactant properties, greater formulating flexibility, in addition to being economically more attractive as compared to products obtained by purification of materials prepared by process of the prior art.

DETAILED DESCRIPTION OF THE INVENTION

The imidazoline starting materials useful in the practice of the invention can be represented by the formula:

FORMULA I

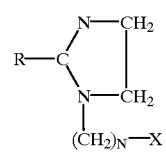

wherein R is an aliphatic radical containing from 5 to 19 carbon atoms per molecule, X is OH or $NH_2$ and $N$ is an integer of from 2 to 4 inclusive. Preferably, R is an aliphatic radical containing a majority of from about 8 to about 18 carbon atoms per molecule, X is OH and $N$ equals 2.

Because of the chemistry involved, compounds of the above formula generally will contain mixtures of different R radicals within the ranges defined above. In one preferred mode of the invention, R is a mixture of saturated and unsaturated aliphatic radicals derived from coconut oil or similar natural oil sources such as palm kernel oil or animal fat sources such as tallow. In that case, each R is a mixture of alkyl radicals containing from about 5 to 18 carbon atoms. In a more preferred material, the mixture of alkyl radicals is derived from a saturated portion of coconut oil or similar natural vegetable oil. In the case of coconut oil fatty acid, each R ranges from about 6 to about 18 carbon atoms. These ranges are given as covering about 90% of the R groups in the compound. Since these R groups are derived from natural sources, they can contain small amounts of other carbon chains. In addition, imidazolines based on single carboxylic acids, e.g., lauric acid, or other cuts, as suited for the particular application, may be used.

The imidazolines used in the present invention should be in substantially pure form. "Substantially pure" is intended to mean substantially free from fatty acids, aminoethylethanol amine, amido esters and diamides. For the purposes of the invention, the presence of amido amines is acceptable. Any convenient method for preparing the imidazoline can be used.

Examples of the starting imidazolines include 2-heptylimidazoline, 2-dodecylimidazoline, 2-heptadecylimidazoline, 1-hydroxyethyl-2-dodecylimidazoline, 1-hydroxyethyl-2-heptadecylimidazoline, and the like. Examples of single fatty acids and fatty acids mixtures that can be used to prepare the imidazolines can include coconut oil fatty acid, palm kernel oil fatty acid, capric, caproic, caprylic, hexadecadienoic, lauric, linoleic, linolenic, margaric, myristic, myristoleic, oleic, palmitic, palmitoleic, stearic and the like.

It is theorized, in the practice of the process of the invention, that the imidazoline is reacted under conditions which will favor opening of the imidazoline ring prior to the alkylation reaction. The reaction is generally conducted in the initial stages to favor ring opening. In one embodiment of the invention, the imidazoline is heated under an elevated pH ranging from about 8.5 to about 10 to facilitate opening of at least a majority of the imidazoline rings. In an alternative embodiment, the imidazoline can be admixed with the monohaloacetate at elevated pH under such conditions that favor ring opening. In a third embodiment, the monohaloacetate is added to the imidazoline along with the addition of base under conditions such that the pH is maintained within the range of about 9 to about 10 during the addition. This theory is presented in an attempt to explain the invention but applicants do not wish to be held to the theory.

In the practice of the invention, the imidazoline is heated with a salt of a monohaloacetate. The haloacetate salt is preferably in aqueous solution prior to admixture with the imidazoline. A convenient method for accomplishing that is to prepare the salt from the acid just prior to the reaction. An advantage to this procedure is that the salt can be prepared with an excess of base to provide neutralization for the hydrohalic acid formed during the reaction of the imidazoline with the haloacetate salt. The excess pH preferably ranges from about 8 to about 10. Of course, haloacetate salt can be purchased or prepared elsewhere, dissolved in water and used as such or preferably with an added amount of base corresponding to the excess discussed above.

Examples of suitable monohaloacetate salts wherein the cationic portion is an alkali metal ion include sodium monochloroacetate, sodium monobromoacetate, and potassium monochloroacetate and potassium-monobromoacetate. The preferred monohaloacetates are the sodium and potassium salts of monochloroacetic acid.

Examples of suitable alkalis that can be used in the process of the invention include sodium hydroxide, potassium hydroxide, sodium carbonate, potassium carbonate, odium bicarbonate, potassium bicarbonate and the like. Preferably, the alkali is sodium and/or potassium hydroxide.

The mole ratio of the monohaloacetic acid or its salt form to the imidazoline or amine is preferably greater than one. At amounts of less than one, insufficient monohaloacetic acid salt is present to effect complete alkylation leaving the product contaminated with the amido amine which has no surface activity. If too high a ratio is used, the product will contain excess glycolic acid since the monohaloacetate salt will react with the base to convert that reactant to glycolic acid. A surprising result of the present invention is that the ratio can be kept as low as possible with only a slight excess needed to drive the reaction to completion while still achieving substantially full alkylation. It is possible by means of the invention to keep the ratio as low as 1.05:1. Preferably the ratio ranges from about 1.05:1 to about 1.5:1, more preferably 1.05:1 to about 1.4:1 and most preferably 1.05:1 to about 1.2:1.

The reaction is generally conducted at a temperature conducive to the reaction as is well known in the industry. Reaction temperatures for the main reaction can range as high as 95° C., preferably between about 50° C. and about 95° C. In one embodiment of the invention temperature as high as about 95° C. were used; in another, temperatures in the range of about 70° to about 80° C. were found effective; and in a third a temperature of about 50° C. was used. More preferably, the temperature ranges from about 75° to about 85° C. The reaction can be heated after the main reaction is considered complete to insure completeness of reaction. Temperatures during this portion of the reaction can range as high as 100° C.

The reaction times are sufficient to accomplish each desired reaction step and can be easily determined by a skilled artisan.

In general, the monohaloacetic acid or salt is blended with the imidazoline at a rate as fast as possible and practical to admix the reactants completely. Because pH control is essential the reactants, especially the base, are added at such a rate as to prevent pH rises above about pH 10. Care is taken to avoid localized "hot spots" during the addition of base. The base is added incrementally to avoid any pH surge.

The careful pH and temperature control during the reaction allows the reaction to proceed with less sodium monohaloacetate salt resulting in a higher purity product (less by-product unalkylated amide, glycolic acid, NaCl and residue haloacetate salt). The compositions of the present invention are characterized by levels of unalkylated amide of less than about 3.5%, preferably less than about 2.0% and more preferably less than about 0.5% unalkylated amide on an actives basis. The compositions of the present invention are also characterized by levels of glycolic acid of less than about 4.5%, preferably less than about 3.5% and more preferably less than about 2.5% glycolic acid on an actives basis. The compositions of the present invention are further characterized by levels of alkali metal salt, e.g., sodium chloride, of less than about 27%, preferably less than about 23% and more preferably less than about 20% salt on an actives basis. Because of the improved purity, the products of the invention exhibit superior surfactant properties, greater formulating flexibility, in addition to being economically more attractive as compared to products obtained by purification of materials prepared by process of the prior art.

The amphoacetate surfactants of the present invention are extremely mild and non-irritating to both eyes and skin.

They also exhibit enhanced wetting speed, greater surface tension reduction, high foaming and foam stabilization properties, low toxicity, and excellent compatibility with other anionic, ionic and nonionic surfactants. These products are stable over a wide pH range and are biodegradable. These properties make these surfactants adaptable for use in products ranging from cosmetics to industrial applications and are usable wherever amphoacetate surfactants of this type have found use. These products are particularly useful for non-irritating shampoos, including baby shampoos, body shampoos including bubble baths, bar soaps, bath gels,. hair conditioning gels, lotions, skin creams and lotions, make up removal creams and lotions, liquid detergents, dish detergents and other washing and cosmetic products that contact the skin.

The present invention is now more fully illustrated in the examples which follow. The percentage purity of the products prepared in the examples and as given in the claims as on a actives basis is by weight based on the amount of active material present in the product determined by subtracting the amount of sodium chloride, glycolic acid and amido amine from the as is solids of the reaction.

EXAMPLE 1

This example illustrates the process of the present invention using different stages of reactant addition.

To a 4-necked round bottom flask equipped with a stirrer, thermometer and dropping funnel was added 465 grams water, 1.6 grams ethylenediaminetetraacetic acid, 207.0 grams (2.19 moles) monochloroacetic acid (99+%) and 366.2 grams of ice. To the flask was slowly added with cooling 218.4 grams (2.73 moles) of 50% sodium hydroxide solution. The temperature is maintained at from 35° to 40° C. during the caustic addition.

Coco imidazoline which has been premelted at a temperature of from 65° to 70° C. in an amount of 504.0 grams (1.81 moles) is added to the reaction vessel as fast as possible. The temperature is kept below 50° C. during the addition which was completed in 20 minutes. The reaction mixture goes through a gel phase before becoming a clear liquid. Reaction temperature is maintained at 50° C. for 2 hours after coco imidazoline addition is complete. The temperature was then raised to 75° C. and caustic was added in three steps.

33.6 grams (0.42 moles) of a 50% sodium hydroxide solution was charged and the reaction mixture held for 15 minutes at 75° C. An additional 33.6 grams (0.42 moles) was charged and held for 15 minutes at 75° C. and then 25.08 grams (0.31 moles) of 50% sodium hydroxide were charged. The pH after these additions was 9.3. The reaction mixture was held at 75° C. for an additional 3 hours. During this time, the reaction pH was determined every 30 minutes.

If the pH was less than 8.5, additional sodium hydroxide was added to elevate the pH to 9.5. After 3 hours, the chloride level was determined, i.e., inorganic chloride divided by the amount of chloride present in the reactants. The ratio is determined by measuring the chloride content in a sample followed by boiling the sample in caustic to liberate any organically bound chlorine, thus determining the total chlorine present in the sample. If the chloride ratio is 0.99, the reaction is considered complete; if less than 0.99, substantially complete alkylation is considered not to have taken place and the reaction is continued at 75° C. When the chloride ratio is 0.99 or above, the reaction was considered completed and the mixture was additionally heated to 90° to 95° C. for 2 hours. After rechecking the chloride ratio, the product was cooled to 60° C. and 146.0 grams of water was charged to a solids content of 44% to 45%.

The product analyzed 43.9% solids, 0.76% glycolic acid, less than 50 ppm sodium monochloroacetate and 6.8% sodium chloride on an as is basis or 2.1% glycolic acid, 18.7% sodium chloride and less than 115 ppm sodium monochloroacetate on a total active basis by weight. Analysis by $_{13}C$ NMR indicated the product to be a compound of Formula II with "R" being coco. Unalkylated amido amines were absent. This was confirmed by capillary gas chromatography performed by spiking with a pure unalkylated material obtained by chromatographic separation. The product showed outstanding surface active characteristics and is expected to exhibit very low irritation characteristics.

The product was evaluated as a foaming agent using the Ross Miles Foam Height Test as outlined in ASTM method D1173 and compared to a commercial product described as Miranol CM from Rhone-Poulenc Inc. The foam was evaluated and the following results were obtained:

| ROSS MILES FOAM HEIGHT AT 25° C. - 0.1% ACTIVE TIME = ZERO | | |
|---|---|---|
| SAMPLE/pH | pH 9.8 | pH 7.1 |
| MIRANOL CM | 14.3 CM | 3.5 CM |
| EXAMPLE 1 | 14.7 CM | 15.3 CM |

| ROSS MILES FOAM HEIGHT AT 25° C. 0.1% ACTIVE - 300 PPM HARD WATER - pH = 7 | | |
|---|---|---|
| SAMPLE/TIME (MIN.) | TIME = ZERO | TIME = 5 MINUTES |
| MIRANOL CM | 2.7 CM | 2.45 CM |
| EXAMPLE 1 | 15.7 CM | 15.6 CM |

It is clear from the above results that the product of the invention, regardless of whether in hard or soft water, provides superior surface activity. In contrast, the commercial product, especially in hard water, shows a reduction in surface activity. This indicates that the commercial product is contaminated with unalkylated material.

EXAMPLE 2

The process of Example 1 was repeated using various mole ratios of sodium chloroacetate to imidazoline. The results reported in Table II below clearly show a reduction in glycolic acid formation and the absence of unalkylated amido amine.

TABLE

| RUN | MOLAR RATIO SMCA TO IMID. | ALKYLATED/ UNALKYLATED CONTENT | ACTIVE | GLYCOLIC ACID % AS IS BASIS/ ACTIVE BASIS | NACL % AS IS BASIS/ ACTIVE BASIS | IMIDO AMINE ACTIVE BASIS |
|---|---|---|---|---|---|---|
| 1 | 1.10 | >99.9  <0.1 | 38.3 | 0.70 (1.83) | 6.45 (16.8) | <0.25 |
| 2 | 1.15 | >99.9  <0.1 | 37.2 | 0.76 (2.04) | 6.5 (17.4) | <0.27 |
| 3 | 1.20 | >99.9  <0.1 | 35.2 | 0.94 (2.67) | 6.8 (19.3) | <0.28 |
| 4 | 1.40 | >99.9  <0.1 | 36.2 | 1.61 (4.45) | 7.1 (19.6) | <0.28 |

EXAMPLE 3

The process of Example 1 was repeated using a controlled addition of NaOH to provide a constant pH during the reaction. Following the addition of the coco imidazoline to the sodium monochloroacetate and after two hours of heating at 75° C., a 50% aqueous solution of sodium hydroxide (92.2 grams. 1.15 moles) was added at a rate sufficient to maintain the pH of the reaction mixture between 9.5 and 10. The pH was monitored by a pH meter. The reaction temperature was held at 75° C. The reaction was held at 75° C. for 1 hour after addition was complete. Analysis by G.C. indicated that the product contained less than 0.2% unalkylated amido amine.

EXAMPLE 4

This example demonstrates the present invention using simultaneous addition of chloroacetic acid and caustic. It is theorized that this procedure converts the imidazoline first to the secondary amine which is then alkylated by slow concurrent addition of alkylating agent and caustic.

To a 5 necked flask equipped with a stirrer, thermometer, two addition funnels and a pH probe was charged 75 grams water and 70 grams (0.25 moles) of coco imidazoline. The reaction mixture was heated to 80° C. To the solution was added simultaneously while maintaining the pH within the range of 9 to 10, 56.7 grams (0.3 moles) of 50% aqueous chloroacetic acid and 40 grams (0.5 moles) of 50% sodium hydroxide solution. The addition required 1 hour. The mixture was stirred for an additional two hours at 80° C. The chloride ratio was 0.99. Analysis by NMR indicated an absence of unalkylated amido amine. This was further confirmed by GC analysis.

EXAMPLE 5

This example demonstrates the procedure wherein the imidazoline is first converted to the secondary amine and then alkylated by slow concurrent addition of alkylating agent and caustic.

Into a 2 liter reaction vessel equipped with two reactant additive pumps, a stirrer operating at about 450 r.p.m. equipped with a PTFE paddle stirrer and shaft, a reaction controller using a glass thermocouple and temperature controller and a low sweep nitrogen sparge, is charged 380 grams (1.38 moles) coco imidazoline, 380 grams water and 2 grams of a 47% solution of sodium hydroxide. The mixture is heated with stirring and nitrogen sparge to 85° C. and over the period of 1 hour after reaching 85° C. the temperature is raised to 95° C. The pH is 9.2. After reaching 95° C., the slow addition of 675 grams of a 25% aqueous solution of sodium monochloroacetate (1.45 moles—mole ratio of 1.05:1) is initiated. The addition rate is 2.8 grams/minute (average of ten reactions) which is equivalent to 5 millimeters/minute. The total addition time is 244 minutes.

Approximately 1 hour after the start of the sodium monochloroacetate feed, 264 grams (1.65 moles—mole ratio 1.19) of a 25% solution of sodium hydroxide is added at an addition rate of 0.9 grams/minute which is equivalent to 5.6 millimeters/minute. The total addition time is 293 minutes. The pH ranged from 9.2 to 9.7 during the addition. Upon completion of the addition, the reaction mixture is heated at 97–100° C. for 2 hours and allowed to cool. The pH is neutralized with hydrocholoric acid. The reaction yielded 1683 grams of product. The product analyzed 36.5% SOLIDS, less than 0.9 unalkylated material, 0.8% glycolic acid and 7.2% sodium chloride on an as is basis by weight based on GC and HPLC analysis. This corresponds to 26.1% sodium chloride, 2.9% glycolic acid and 3.3% unalkylated material on an actives basis.

EXAMPLE 6

Into a glass lined reactor equipped with an agitator, a condenser, nitrogen purge/flush, steam heating, water cooling, and two metering pumps is charged 225 parts coco imidazoline (average molecular weight 268), 200 parts water and 2 parts of a 25% solution of sodium hydroxide. The mixture is heated with steam until a temperature of 85° C. is reached and then further steam is intermittently applied over the period of 1 hour until the temperature is slowly raised to 95° C. After reaching 95° C., the slow addition of 445 parts of a 25% aqueous solution of sodium monochloroacetate (mole ratio of 1.2:1/SMCA:imidazoline) is initiated. The average addition rate is 95 parts/hour. One hour after the initiation of the SMCA feed, the addition of 150 parts of a 25% aqueous solution of sodium hydroxide (1.19 molar equivalents) is commenced. The sodium hydroxide solution is incrementally fed at an approximate rate of 16 parts per hour using a modulated addition means in order to maintain the pH within the range of from 8.5 to 9.5.

The temperature is maintained at 95° C. throughout the reaction except that the temperature was elevated to 98° C. for one hour at the end of the reaction to convert remaining SMCA to glycolic acid.

After neutralization, the following analysis is obtained:

| Solids | 35.9% |
|---|---|
| pH (20%) | 8.42 |
| Color (2 Gardner) Lovibond | 11Y–2.2R |

| | AS IS BASIS | ACTIVES BASIS |
|---|---|---|
| NaCl | 7.19 | 26.5 |
| Amido Amine | .86 | 3.2 |
| SMCA | <5 ppm | |
| Glycolic Acid | 0.8 | 2.95 |
| Nitrogen | 2.2 | |

EXAMPLE 7

This is a comparative example showing the effect of not following the invention has on the presence of unalkylated species. To 116.6 grams (1.0 moles) sodium chloroacetate in 350 grams water was added 92.8 grams (1.16 moles) 50% sodium hydroxide solution. The reaction temperature was adjusted to 35° C. and 278 grams (1.0 moles) coco imidazoline was added rapidly. The temperature of the reaction mixture was 85° to 90° C. and maintained at that temperature for 3 hours. The clear liquid was adjusted to 45% solids and analyzed. The product contained unalkylated amido amine by gas chromatographic analysis. The ratio of alkylated product to unalkylated product is 75/25.

EXAMPLE 8

This is a comparative example using Example 1 of U.S. Pat. No. 4,269,730. This patent teaches that the reaction between the imidazoline and the chloroacetate salt is conducted under pH 9 (pH 7.5–8.5) to provide a cyclic betaine which is stable at pH's below 9. The reactions taught in this patent are run to prepare the betaine by keeping the pH only slightly alkaline.

The procedure of Example 1 of U.S. Pat. No. 4,269,730 was followed using the conditions recited therein. The product was analyzed by G.C. and was found to contain alkylated amido amine in a ratio to unalkylated amido amine of about 85/15. A second experiment using a mole ratio of 1.2:1 sodium monochloroacetate to imidazoline produced a product showing a ratio of alkylated product to unalkylated amido amine (by G.C. analysis) of 70/30.

What is claimed is:

1. A process for the preparation of an amphoacetate surfactant consisting essentially of the steps of reacting an alkylimidazoline or an open-ring derivative thereof with a monohaloacetic acid or a salt thereof in the presence of a base under conditions such that the pH of the reaction mixture during the reaction is in the range of from about 8.5 to about 10.

2. A process as recited in claim 1 wherein the imidazoline is a compound represented by the formula:

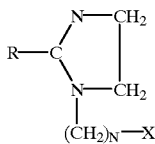

wherein R is an aliphatic radical containing from 5 to 19 carbon atoms per molecule, X is OH or NH$_2$ and $_N$ is an integer of from 2 to 4 inclusive.

3. A process as recited in claim 2 wherein X is OH.

4. A process as recited in claim 2 wherein R is derived from a member selected from the group consisting of coconut oil fatty acids, palm kernel oil fatty acids, capric, caproic, caprylic, hexadecadienoic, lauric, linoleic, linolenic, margaric, myristic, myristoleic, oleic, palmitic, palmitoleic, and stearic acids and mixtures thereof.

5. A process as recited in claim 1 wherein the alkylimidazoline is a coco imidazoline.

6. A process as recited in claim 1 wherein the monohaloacetic is the sodium salt of monochloroacetic acid.

7. A process as recited in claim 1 wherein the base is selected from the group consisting of sodium hydroxide, potassium hydroxide, sodium carbonate, potassium carbonate, sodium bicarbonate, potassium bicarbonate and mixtures thereof.

8. A process as recited in claim 1 wherein the pH during the reaction is maintained at an amount within a pH range of from about 8.5 to about 9.5.

9. A process as recited in claim 1 wherein the reaction is conducted at a temperature within the range of from about 75° to about 85° C.

10. A process as recited in claim 1 wherein the ratio of haloacetic acid or a salt thereof to alkylimidazoline ranges from about 1.05:1 to about 1.5:1.

11. A process as recited in claim 2 wherein R is an aliphatic radical containing from 5 to 19 carbon atoms per molecule, X is OH and $_N$ is an integer of 2, M is sodium, the alkali is sodium and/or potassium hydroxide and the temperature ranges from about 50° C. to about 95° C.

12. A process as recited in claim 1 wherein a majority of the imidazoline is in the open ring form at the point of reaction.

13. A process as recited in claim 12 wherein the pH during the reaction is maintained at an amount within a pH range of from about 8.5 to about 9.5.

14. A process as recited in claim 12 wherein the alkylimidazoline is a coco imidazoline.

15. A process as recited in claim 12 wherein the monohaloacetic is the sodium salt of monochloroacetic acid.

16. A process as recited in claim 12 wherein substantially all of the alkylimidazoline is an open ring derivative.

17. A process for the preparation of an amphoacetate surfactant comprising:
    a) reacting an alkylimidazoline with heat at a pH ranging from about 8.5 to about 9.5 to form an open ring derivative of said alkylimidazoline
    b) reacting said open ring derivative of said imidazoline with a monohaloacetic acid or a salt thereof in the presence of an base under conditions such that the pH of the reaction mixture during the reaction is from about 8.5 to about pH 10 and
    c) recovering said amphoacetate surfactant.

18. A process for the preparation of an amphoacetate surfactant comprising:
    a) reacting an alkylimidazoline with heat at a pH ranging from about 8.5 to about 9.5 for a period of time sufficient to open a majority of the alkylimidazoline rings,
    b) the product of step a) with a monohaloacetic acid or a salt thereof in the presence of an alkali under conditions such that the pH of the reaction mixture during the reaction does not exceed a pH above about pH 10, the temperature of the reaction ranging from about 50° C. to about 95° C., and
    c) recovering said amphoacetate surfactant.

19. The process of claim 17 wherein the temperature of the reaction ranges from about 50° C. to about 95° C.

20. A process for the preparation of an amphoacetate surfactant consisting essentially of the steps of:
    i) reacting a fatty acid with aminoethylethanolamine to form an alkyl imidazoline;
    ii) reacting said alkylimidazoline with heat at a pH ranging from about 8.5 to about 10 to form an open-ring derivative of said alkylimidazoline;
    iii) reacting said open-ring derivative of said alkylimidazoline with a monohaloacetic acid or a salt thereof in the presence of a base under conditions such that the pH of the reaction mixture during the alkylation reaction remains in the range of from about 8.5 to about 10; and
    iv) recovering the amphoacetate surfactant product of said alkylation reaction.

21. A process for the preparation of an amphoacetate surfactant consisting essentially of the steps of:

i) reacting a natural oil with aminoethylethanolamine to form an alkylimidazoline;

ii) reacting said alkylimidazoline with heat at a pH ranging from about 8.5 to about 10 to form an open-ring derivative of said alkylimidazoline;

iii) reacting said open-ring derivative of said alkylimidazoline with a monohaloacetic acid or a salt thereof in the presence of a base under conditions such that the pH of the reaction mixture during the alkylation reaction remains in the range of from about 8.5 to about 10; and iv) recovering the amphoacetate surfactant product of said alkylation reaction.

* * * * *

UNITED STATES PATENT AND TRADEMARK OFFICE
CERTIFICATE OF CORRECTION

PATENT NO. : 5,952,291
DATED : Sep. 14, 1999
INVENTOR(S) : Desai et al.

Page 1 of 5

It is certified that error appears in the above-identified patent and that said Letters Patent is hereby corrected as shown below:

In column 1, at lines 52 to 56, delete

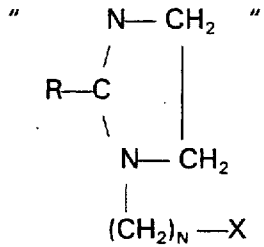

and insert

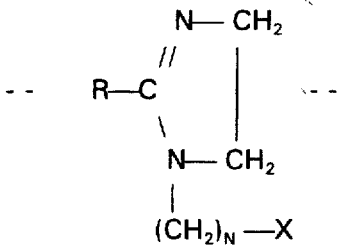

UNITED STATES PATENT AND TRADEMARK OFFICE
CERTIFICATE OF CORRECTION

PATENT NO. : 5,952,291
DATED : Sep. 14, 1999
INVENTOR(S) : Desai et al.

Page 2 of 5

It is certified that error appears in the above-identified patent and that said Letters Patent is hereby corrected as shown below:

In column 2, at lines 11-16, delete

"
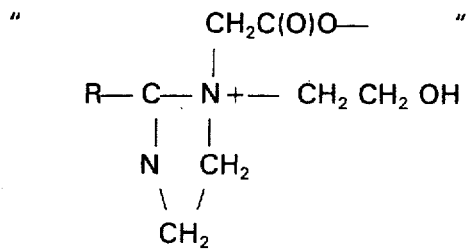
"

and insert

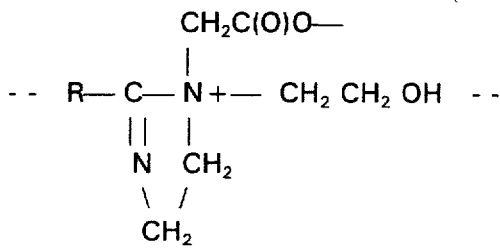

UNITED STATES PATENT AND TRADEMARK OFFICE
CERTIFICATE OF CORRECTION

PATENT NO.   : 5,952,291
DATED        : Sep. 14, 1999
INVENTOR(S)  : Desai et al.

It is certified that error appears in the above-identified patent and that said Letters Patent is hereby corrected as shown below:

In column 2, at lines 32-38, delete

" 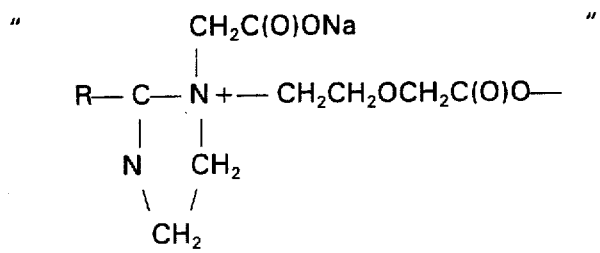 "

and insert

-- 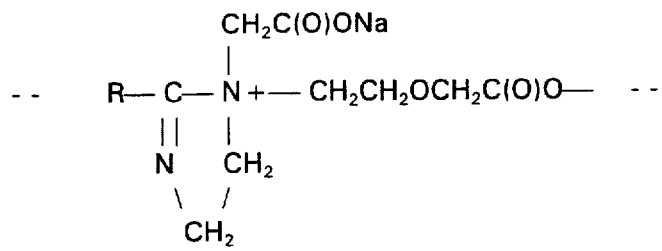 --

UNITED STATES PATENT AND TRADEMARK OFFICE
CERTIFICATE OF CORRECTION

PATENT NO. : 5,952,291
DATED : Sep. 14, 1999
INVENTOR(S) : Desai et al.

It is certified that error appears in the above-identified patent and that said Letters Patent is hereby corrected as shown below:

In column 4, at lines 52-57, delete

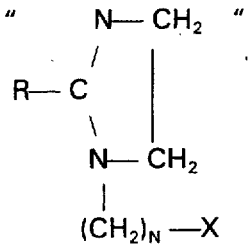

and insert

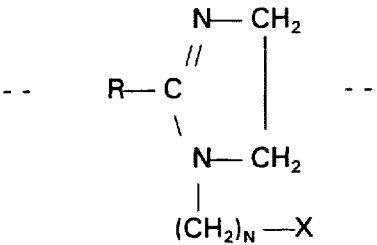

UNITED STATES PATENT AND TRADEMARK OFFICE
CERTIFICATE OF CORRECTION

PATENT NO. : 5,952,291
DATED : Sep. 14, 1999
INVENTOR(S) : Desai et al.

It is certified that error appears in the above-identified patent and that said Letters Patent is hereby corrected as shown below:

In claim 2, at line 3 thereof, delete

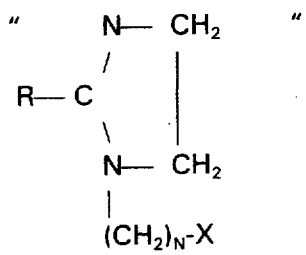

and insert

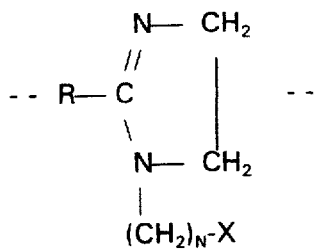

Signed and Sealed this

Twentieth Day of June, 2000

Attest:

Q. TODD DICKINSON

Attesting Officer     Director of Patents and Trademarks